United States Patent [19]

Watanabe et al.

[11] Patent Number: 5,074,156
[45] Date of Patent: Dec. 24, 1991

[54] FLOW CONTROL MECHANISM FOR AUTOMATIC PRESSURE REDUCING EQUIPMENT

[75] Inventors: Toshikazu Watanabe; Toshio Ichinose, both of Tokyo, Japan

[73] Assignee: Nikkiso Co., Ltd., Tokyo, Japan

[21] Appl. No.: 448,372

[22] Filed: Dec. 11, 1989

[51] Int. Cl.⁵ ............................................. G01N 1/00
[52] U.S. Cl. .................................................. 73/864.81
[58] Field of Search ............ 73/863.81, 863.86, 864.81; 376/245

[56] References Cited

U.S. PATENT DOCUMENTS

| | | | |
|---|---|---|---|
| 3,365,951 | 1/1968 | Jentzsch et al. | 73/864.81 |
| 3,985,624 | 10/1976 | Prevost et al. | 73/863.81 |
| 4,882,122 | 11/1989 | Head et al. | 376/245 |

FOREIGN PATENT DOCUMENTS 0038679  8/1987  Japan .................................. 376/245

Primary Examiner—Robert Raevis
Attorney, Agent, or Firm—Young & Thompson

[57] ABSTRACT

A simplified and easily operative flow control mechanism for an automatic pressure reducing equipment characterized in that a pressure detector detects such an inconvenient condition that a pressure of high pressure sample water is extremely reduced on an inlet line of a pressure reducing mechanism until the pressure reducing mechanism becomes inoperable, and that pressure-reduced sample water can bypass a flow control valve being provided on an outlet line of the pressure reducing mechanism by an automatic opening operation of an electromagnetic control valve so as to feed a predetermined amount of the sample water to an analysis system.

1 Claim, 7 Drawing Sheets

FLOW CONTROL MECHANISM FOR AUTOMATIC PRESSURE REDUCING EQUIPMENT

FIELD OF THE INVENTION

This invention relates to an automatic pressure reducing equipment, particularly to a flow control mechanism for the automatic pressure reducing equipment. According to the flow control system for the automatic pressure reducing equipment, upon taking high pressure sample water in a sampling equipment for thermal power and nuclear power plants, a pressure in an outlet of the pressure reducing equipment can be constantly kept constant irrespective of change in an original pressure of the sample water. Also, even though the original pressure of the sample water becomes extremely lowered so as to eliminate an automatic pressure reducing function, a predetermined flow rate of the sample water can be maintained successively.

BACKGROUND OF THE INVENTION

In facilities of the thermal and nuclear power plants, a pressure reducing mechanism is employed in order to constantly keep a flow rate of the sample water constant when high-pressure sample water is taken from a given portion of a circulating system for a boiler water and led to a water quality analyzer.

Conventionally, there has been proposed a pressure reducing mechanism a pressure reducing constant of which is maintained to be fixed. The pressure reducing mechanism has such a disadvantage that an outlet flow rate is varied as an original pressure of sample water changes.

In order to vary automatically the pressure reducing constant in response to a change of the original pressure of the sample water, there has also been proposed, as seen in FIG. 5, another flow control mechanism comprising a regulating lever 516 inserted into a pressure reducing mechanism 514, a fluid control cylinder 518 constituted by connecting one end of the regulating lever 516 to a spool 520, a flow control valve 522 for operating the fluid control cylinder 518, and a controller 528 for controlling the flow control valve 522 on the basis of a signal for contact operation generated by a pressure detector 526, as disclosed in Japanese Patent Publication No. 56-12806.

However, this type of the automatic pressure reducing mechanism has many structural problems such as a control delay due to a fluid pressure control, a low accuracy of positioning and a fluctuation in the pressure reducing constant due to leakage at a gland point of the adjusting lever and the like.

From the above viewpoint, there has also been proposed, as seen in FIG. 6, a pressure reducing mechanism 610 for sampling equipment, comprising two tubules 614 and 616 for effecting pressure control, each of which is provided on one end thereof with a fitting connected to a sample water line 612 and on the other end with a fitting 618 connected to a pressure control line 620, core rods 636 and 638, moving back and forth in the tubules 614 and 616, respectively, by drive means 634 for a feed screw 622 inserted into the pressure control line 620. A handle 646 can be manipulated to adjust the position of the feed screw 622 from outside the pressure reducing mechanism 610, as disclosed in Japanese Utility Model Publication No. 56-12592.

In such a pressure reducing mechanism, as well as conventional control mechanisms being used in general, when controlling the core rod inserted into the pressure control tubule by means of the feed screw, an automatic operation for controlling it at a high speed and with a high accuracy can not be realized even though no structural problems such as the fluctuation in the pressure reducing constant due to the leakage, etc. is caused.

The present inventors have developed an automatic pressure reducing equipment which is disclosed in Japanese Laid-Open Patent Publ. No. 57-100336. In that equipment, a pressure reducing mechanism (10) comprises inlet and outlet pressure control tubules (20, 24) into each of which is inserted a core rod (26, 28) supported by a movable ring (30). Into the movable ring (30) is screwed a threaded shaft (32) which is movably supported in the pressure reducing line. The pressure reducing mechanism (10) is connected to a sample water line (22) so as to detect a sample water pressure on the outlet side and keep the outlet pressure equal to the present one by adjusting the threaded shaft (32). Also, the pressure reducing mechanism (10) is provided on the outlet-side sample water line (22) with a pressure transducer (64) for generating a pressure signal and with a proportional controller (70) for transmitting an operation signal to a servo motor (36) after comparing the pressure signal with the preset pressure. A gear (40) is provided on a revolving shaft (42) derived through a reducer (38) from the servo motor (36) in order to engage another gear (52) provided on one end of the threaded shaft (32). Furthermore, a potentiometer (58) for detecting the number of revolutions of the servo motor (36) is provided so as to indicate an insertion of the core rods (26, 28) (see FIGS. 7 to 9).

Since, in the above-mentioned conventional pressure reducing mechanism which used two tubules for pressure control and the core rods being movable back and forth in the tubules, there is only extremely narrow clearance therebetween, the sample water may be prevented from passing through the clearance or a movement of the core rods in the tubules may be interrupted due to an accumulation of impurities contained in the sample water and an entrance of sludge into the clearance and the like. On the other hand, the core rods are fixedly connected to a common movable member in the pressure control line. The movable member is provided with a threaded hole so as to fit the feed screw thereinto. The core rods can be moved together with the movable member by rotating the feed screw from the outside of the tubule. Accordingly, in case the core rods are stopped from moving back and forth in the tubule due to the reasons hereinbefore described, the movable member can not move in the axial direction of the threaded shaft. As a result, the movable member is forced to rotate together with the feed screw so that a pair of parallel core rods may be warped to be broken or become useless, whereby the pressure control tubules may be damaged. Further, in this pressure reducing equipment, a position of the core rod is detected on the basis of the number of revolutions of the feed screw because rotary drive is converted into reciprocating motion. Therefore, in order that the core rods are more accurately positioned in the pressure control tubules, a conversion coefficient must be strictly determined. However, some errors can be inevitably generated due to instrumental error, etc. so that a high precision positioning of the core rods can not be easily performed. Furthermore, in a conventional pressure reducing equipment, the pressure control tubules, a pressure control line and core rods are always designed with a constant relation therebetween and manufactured integratedly. Accordingly, even if any part of these components are broken or damaged, all of them must be replaced. Also, in case of changing a control range of a pressure reducing condition, the respective control ranges of all components must be changed. Thus, an amount of cost for a maintenance and a design change is extremely increased. Moreover, upon replacing operation of such a pressure reducing equipment, a line system for the sample water with a high pressure must be stopped to separate the pressure reducing equipment therefrom so that a great deal of time and labor is required for the replacement.

The applicants of the invention have now developed a pressure reducing mechanism for the automatic pressure reducing equipment which can realize a convenient maintenance and an improved control performance, and then filed a Japanese patent application regarding the pressure-reducing control mechanism. The pressure reducing control mechanism comprises the pressure control tubules, the core rods and the pressure control pipe members which can be separated from each other. The adjustment of a position of the core rods is effected together with detection of the position by using a linear control means for making rectilinear motion. Therefore, it is possible to facilitate a manufacturing process of the pressure reducing equipment and enhance the precise positioning of the core rods to effect a strict pressure reducing control.

Namely, the pressure reducing control mechanism for the automatic pressure reducing equipment comprising the first pressure control pipe member having a pair of pressure control tubules parallel to each other, on one end of each of which a connector communicating with the pressure control tubule is provided in order to be connected to an external line and from the other end of each of which the core rod being movable back and forth is inserted into the pressure control tubule, the second pressure control pipe member fluid-tightly connected to the other end of the first pressure control pipe member through a fixture, in which a slide lever is insertedly arranged such that one end of the slide lever is provided with a connecting member disconnectably attached to the core rods and the other end is sealed with a gland packing, and a control means for adjusting the positioning of the core rods in the pressure control tubules through the slide lever by motor-driving and reciprocating a rack lever, the rack lever being arranged parallel to the slide lever and connected on its one end through a connecting member to a tip portion of the slide lever.

However, in a conventional automatic pressure reducing equipment the automatic pressure reducing control is required to keep a constant pressure and flow rate suitable for feeding the sample water to an analysis system despite of a fluctuation in the original pressure of the sample water. For this reason, the conventional equipment employs an automatic pressure-reducing control system shown in FIG. 4. As shown in FIG. 4, reference numerals 10 and 12 represent the pressure reducing mechanism and an automatic pressure-reducing control unit for controlling the pressure reducing mechanism, respectively. The pressure reducing mechanism 10 is provided with an inlet 14a for feeding the sample water and an outlet 14b for discharging the sample water. The inlet 14a and outlet 14b are connected to an inlet line 16 for feeding the high pressure sample water to the pressure reducing mechanism and an outlet line 18 for discharging the pressure-reduced sample water therefrom, respectively. The inlet line 16 is provided with an inlet control valve 20 which is opened or closed by manually entering an open/close command signal while being automatically opened or closed under a constant pressure condition. The outlet line 18 is provided with a flow control valve 22 formed as a needle valve so as to communicate with the analysis system for the sample water. A relief valve 24 and a pressure detector 26 are connected to the outlet line 18 on the upstream side of the flow control valve 22. A pressure of the sample water is detected by the pressure detector 26. A signal of the detected pressure is transferred to a controller 28 which compares a preset value of the pressure with the detected value thereof to calculate a deviation between the two values. In order to perform a pressure control according to the calculated deviation, the controller 28 transmits to the automatic pressure-reducing control unit 12 a control command for adjusting a position of the core rods in the pressure reducing mechanism 10.

In case that such a conventional flow control system for the pressure reducing sample water is operated by a command of an automatic mode and the high pressure sample water within a permissible range of pressure is fed to the inlet line 16, the automatic pressure-reducing control unit 12 can perform an appropriate pressure-reducing feedback control through the controller 28. However, for example, if a pressure of the high pressure sample water is reduced below the permissible range and then the pressure reducing mechanism 10 is led to the minimum pressure-reducing (a pressure reducing value 0), the flow control valve 22 comprising the needle valve is rendered closed due to a shortage of the pressure of the sample water on the outlet line 18 so that the sample water is stopped to be fed to the analysis system. On the other hand, when the pressure of the sample water to be fed to the inlet line 16 is lowered, the inlet control valve 20 is automatically closed. In this case, even if the inlet control valve 20 is manually opened, the flow control valve 22 remains closed as long as the pressure of the sample water continues to be lowered.

Thus, when the original pressure of the high pressure sample water is lowered due to any causes, a continuous analysis of the sample water is essential to solution to the causes, particularly to a safety operation of thermal/nuclear power plants. Therefore, as described hereinbefore, it is required to improve the pressure reducing mechanism of the automatic pressure reducing equipment such that the pressure-reduced sample water can be fed to the analysis system even if the original pressure of the sample water is extremely lowered to eliminate a pressure reducing function of the pressure reducing mechanism.

SUMMARY OF THE INVENTION

Accordingly, it is an object of this invention to provide a simplified and easily operative flow control mechanism for an automatic pressure reducing equipment. In the flow control mechanism, when a pressure of a high pressure sample water is extremely reduced on an inlet line of the pressure reducing mechanism until the pressure reducing mechanism is rendered inoperable, a pressure detector detects such an inconvenient condition. In this case, the pressure-reduced sample water can bypass a flow control valve provided on an outlet line of the pressure reducing mechanism, by an automatic opening operation of the electromagnetic control valve. Thus, a predetermined amount of the sample water can be fed to an analysis system.

In accordance with this invention, there is provided a flow control mechanism for the automatic pressure reducing equipment. The automatic pressure reducing equipment has a pressure reducing mechanism comprising a pair of pressure control tubules parallel to each other, an inlet line for feeding high pressure sample water and an outlet line for discharging pressure-reduced sample water being connected to one end of each of the pressure control tubules and a pair of core rods being inserted into the other end of each of the pressure control tubules, an automatic pressure-reducing control unit for automatically adjusting a position of the core rods to be inserted into the pressure control tubules, and a controller for generating a control command to the automatic pressure-reducing control unit such that a pressure of the sample water being detected in the outlet line is controlled so as to be equal to a preset value after detecting the pressure of the sample water. The flow control mechanism for the automatic pressure reducing equipment is characterized by;

a manifold being provided to the outlet line, from a part of which the outlet line is derived and communicates through a main flow control valve with an analysis system for the sample water;

a pressure detector and a relief valve being connected to the manifold;

a bypass line being derived from a part of the manifold and communicating through an electromagnetic control valve and an auxiliary flow control valve with a downstream side of the outlet line being provided with the main flow control valve; and a control means for opening the electromagnetic control valve when the main flow control valve is closed due to a reduction of a pressure of the sample water in the outlet line.

In the flow control mechanism, the control means for opening the electromagnetic control valve comprises the controller and the pressure detector arranged on the manifold. The detector detects a pressure of the sample water in the outlet line. When a detected value of the pressure of the sample water is decreased below a value of the minimum pressure-reducing in the pressure reducing mechanism, the controller generates a control command for opening the electromagnetic control valve.

According to the invention, in the flow control mechanism for the automatic pressure reducing equipment which has the pressure reducing mechanism, the automatic pressure-reducing control unit and the controller, a manifold for feeding the pressure-reduced sample water through the main flow control valve to the analysis system is provided on the outlet line derived from the pressure reducing mechanism. The manifold is connected to the bypass line bypassing the main flow control valve through the electromagnetic control valve and the auxiliary flow control valve while being appropriately connected to the pressure detector and the relief valve. Therefore, in case an original pressure of the high pressure sample water on the inlet line is extremely reduced until the pressure reducing mechanism is rendered inoperable, the pressure detector detects such an inconvenient condition so that the electromagnetic control valve can be automatically opened.

To this end, a predetermined amount of the sample water can be continuously fed through the bypass line to the analysis system for the sample water even though the main flow control valve is closed due to a pressure reduction of the sample water on the outlet line.

BRIEF DESCRIPTION OF THE DRAWINGS

Preferred embodiments of the present invention will be described hereinafter in detail with reference to the accompanying drawings in which.

PREFERRED EMBODIMENTS OF THE INVENTION

Figure 1:
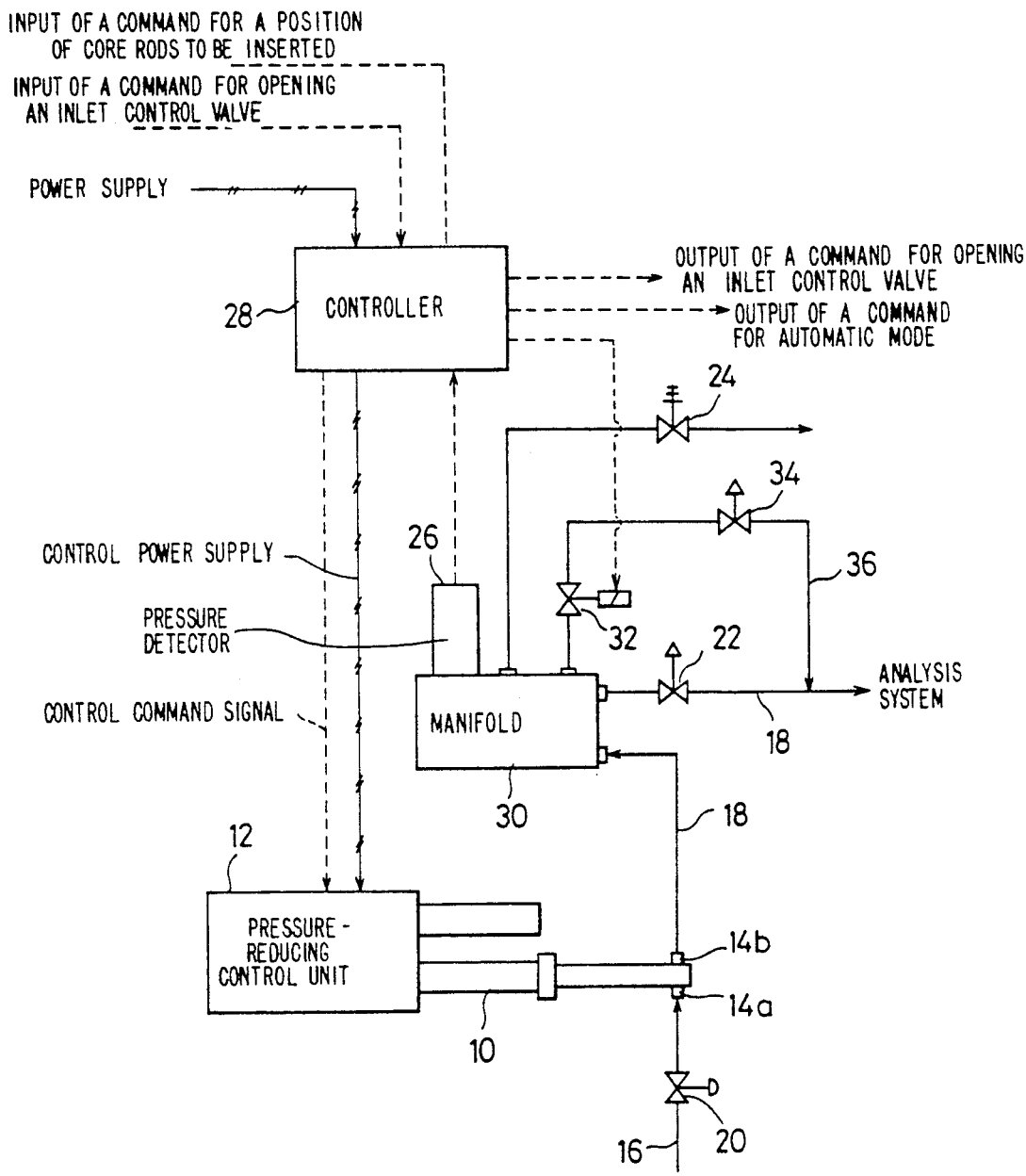
FIG. 1 is a control system diagram of a flow control mechanism for an automatic pressure reducing equipment according to one embodiment of the present invention.
Figure 4:
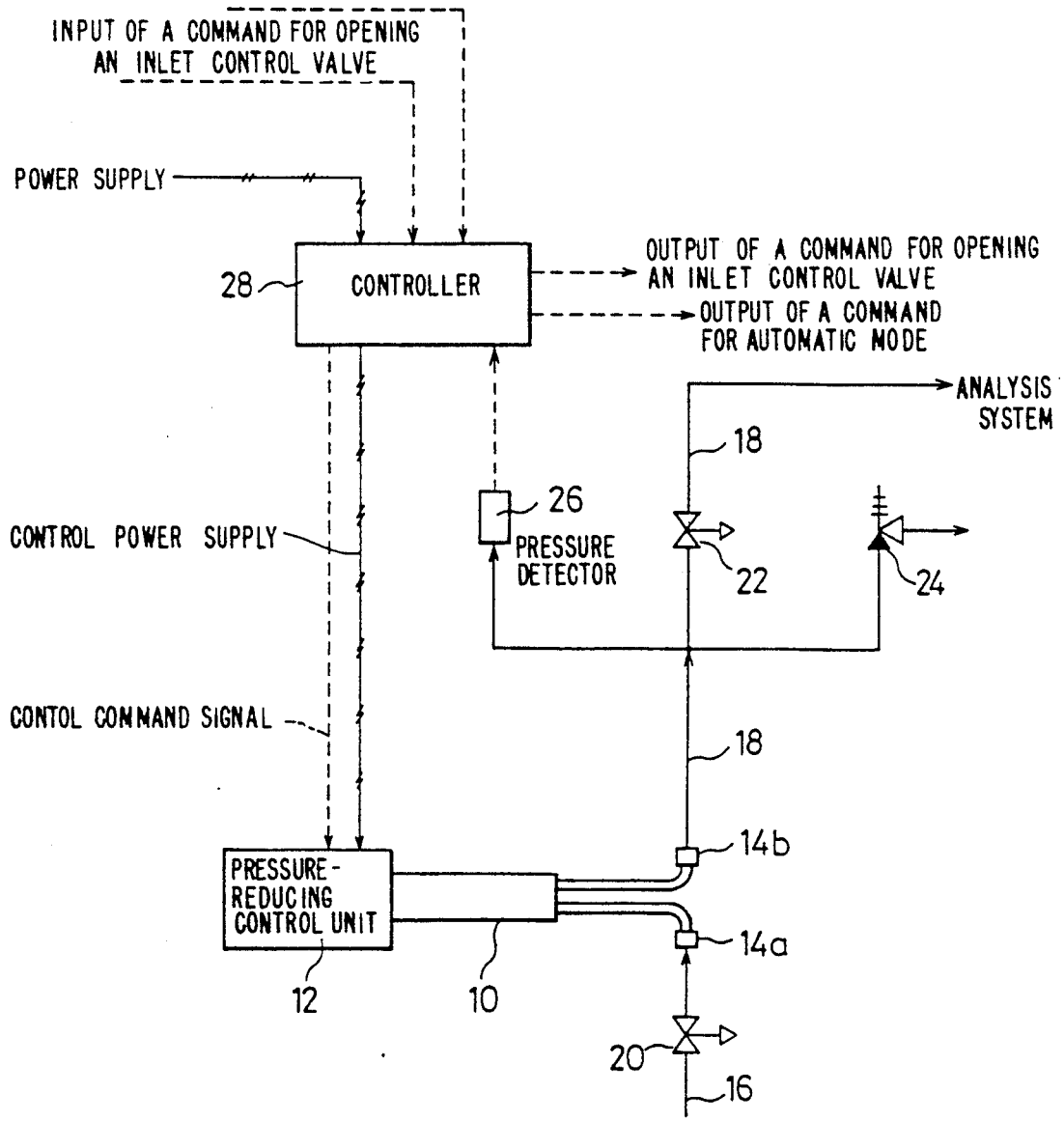
FIG. 4 is a control system diagram showing a system structure of a flow control mechanism for a conventional automatic pressure reducing equipment.
Figure 5:
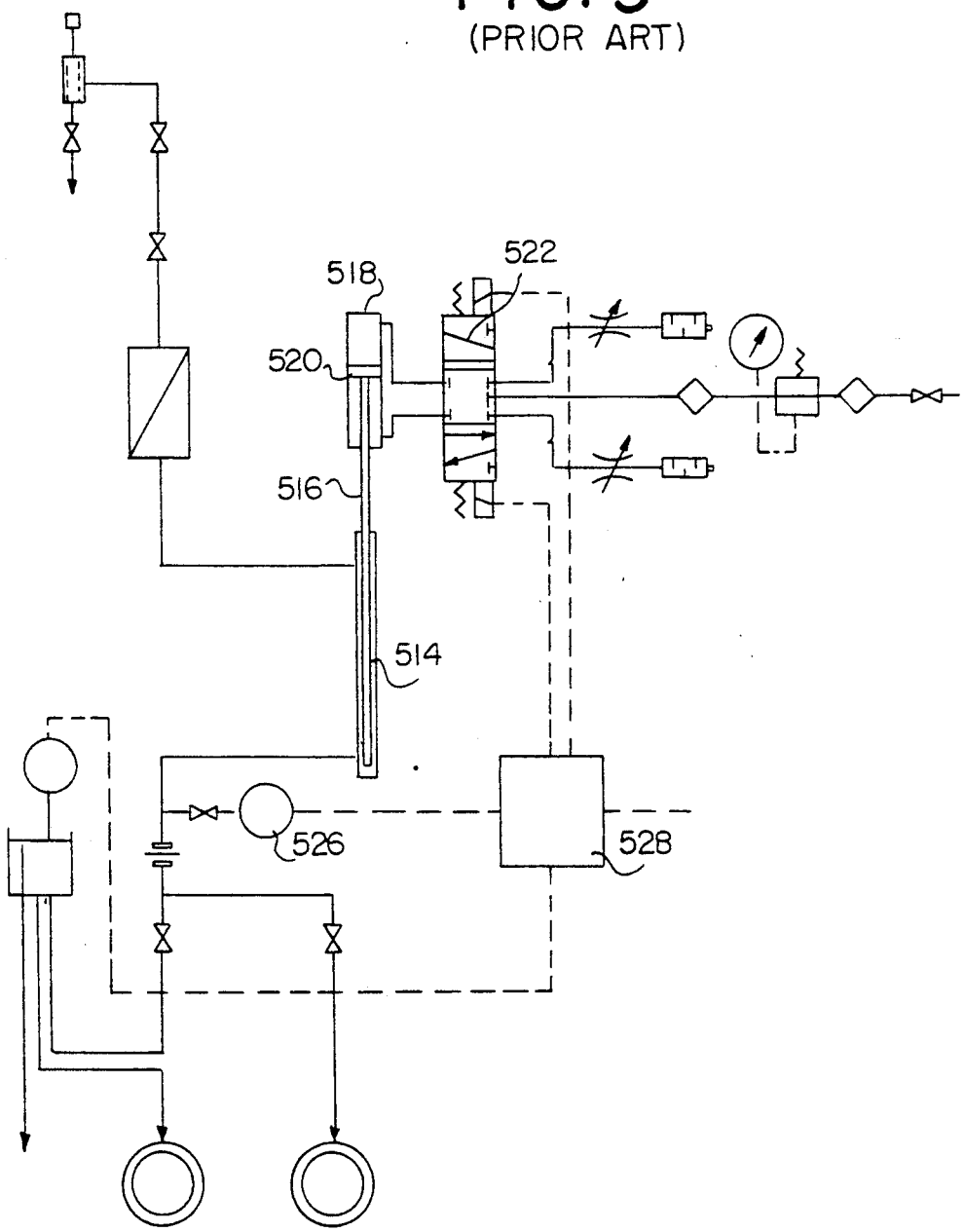
FIGS. 5-9 are view illustrating the prior art discussed above.
Figure 6:
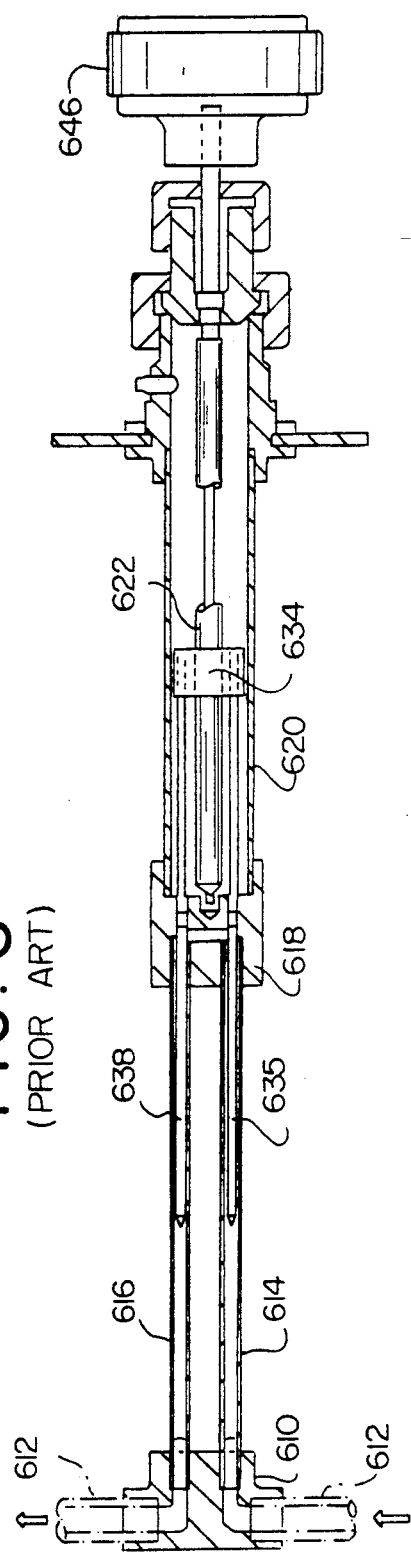
Figure 7:
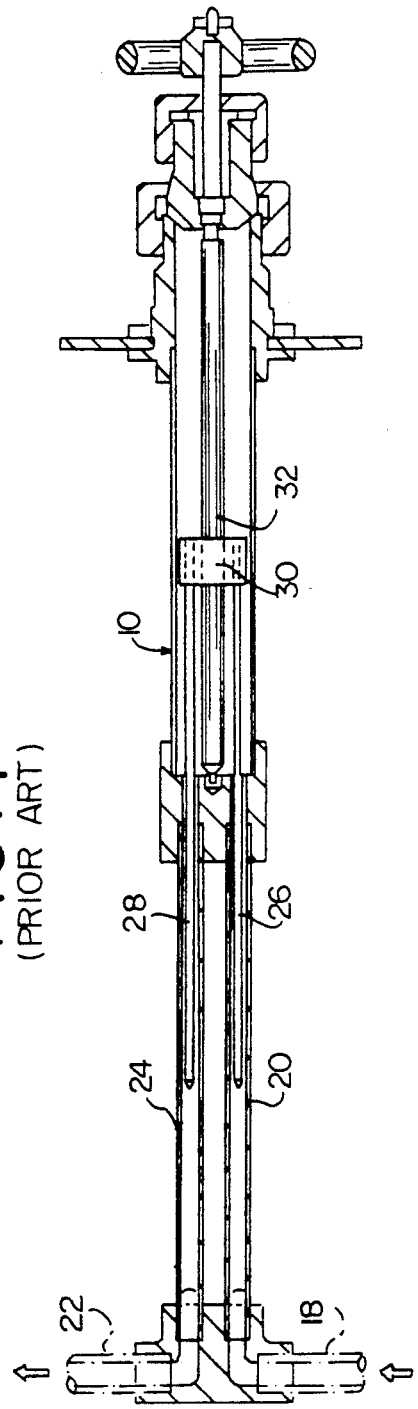
Figure 8:
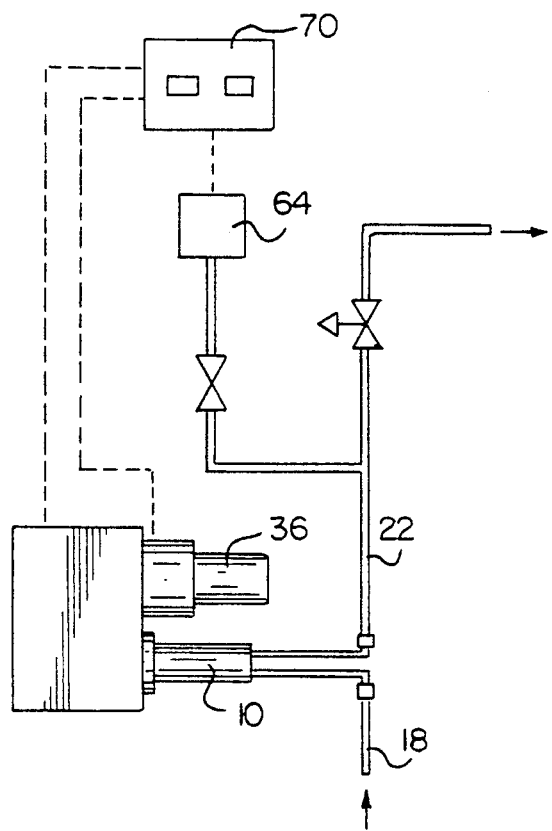
Figure 9:
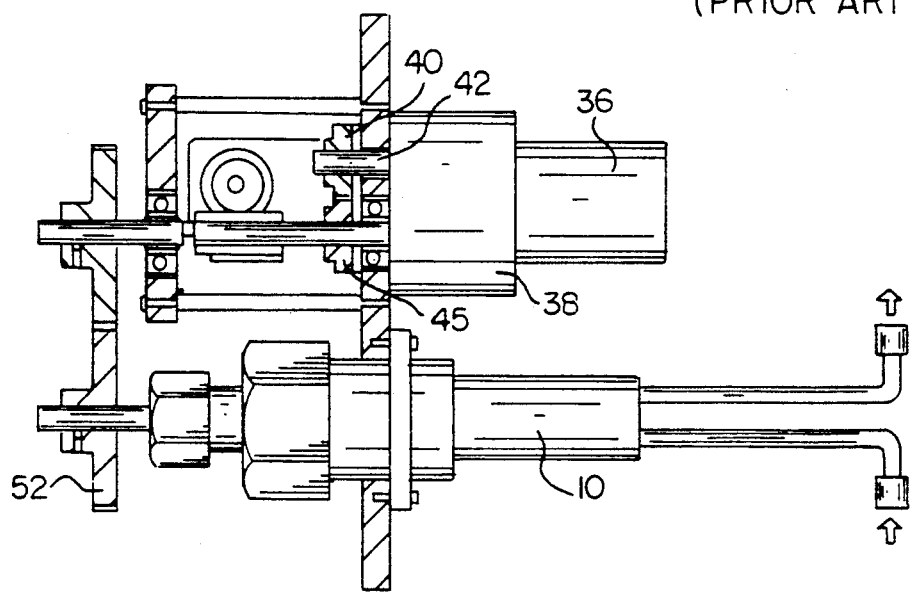

FIG. 1 is a system diagram of an automatic pressure reducing control system for a flow control mechanism according to one embodiment of the present invention. As a matter of descriptive convenience, like reference numerals refer to like parts without a detailed explanation of the respective parts in a conventional automatic pressure reducing control system shown in FIG. 4. In FIG. 1, a pressure reducing mechanism 10 according to the embodiment has a pair of pressure reducing tubules parallel to each other. An inlet line for feeding high pressure sample water and an outlet line for discharging pressure-reduced sample water are respectively connected to one end of each of the pressure reducing tubules. A pair of core rods for pressure reducing are respectively inserted into the other end of each of the pressure reducing tubules such that a position of the core rods can be freely adjusted in order to equalize a pressure value of the pressure-reduced sample water on the outlet line to a preset value. A pressure control system having the same structure as this embodiment may be effectively available in both the pressure reducing mechanism previously proposed by the present applicants and a conventional pressure reducing mechanism. An automatic pressure-reducing control unit 12 is constituted such that an inserting position of the core rods provided in the pressure reducing mechanism 10 can be automatically adjusted by a motor-driven control.

In this embodiment, respective connectors 14a and 14b communicating with a pair of pressure control tubules in the pressure reducing mechanism 10 are connected to the inlet line 16 and the outlet line 18. The inlet line 16 is provided with an inlet control valve 20 in the same manner as a conventional equipment. On the other hand, the outlet line 18 is provided with a manifold 30 having a necessary volume. A flow control valve 22 formed as a needle valve is provided in the outlet line 18 which is derived from a part of the manifold 30 and communicates with an analysis system for the sample water. Further, the manifold 30 is connected to a relief valve 24 and a pressure detector 26 in the same manner as that in a conventional automatic pressure-reducing control system. Namely, a pressure of the sample water is detected by the pressure detector 26 and a pressure signal is transferred to a controller 28. The controller 28 compares a preset value of a pressure of the sample water with a detected value thereof so as to calculate a deviation therebetween. In order to perform a pressure control on the basis of the deviation, a control command for adjusting the position of the core rod arranged in the pressure reducing mechanism is transferred to the automatic pressure-reducing control unit 12.

The structure described hereinbefore is basically the same as that of an automatic pressure reducing control system in a conventional equipment. Then, according to the present invention, a manifold 30 is provided at a part of the outlet line 18 Further, a bypass line 36 is connected to a part of the manifold 30 so as to communicate, through an electromagnetic valve 32 and an auxiliary flow control valve 34 formed as a needle valve, with the downstream side of the outlet line 18 being provided with the flow control valve 22. The electromagnetic valve 32 is opened by a command transmitted through a controller 28, when the pressure detector 26 detects a pressure of the sample water on the outlet line 18 in such an irregular state that the pressure reducing mechanism 10 is led to the minimum pressure-reducing, by which the mechanism is rendered inoperable. The auxiliary flow control valve 34 is formed as a needle valve as well as the flow control valve 22 provided on the outlet line 18, an operative pressure of the auxiliary flow control valve 34 is set to a sufficiently low pressure. Thus, as described above, the bypass line 36 is automatically connected when the original pressure of the high pressure sample water on the inlet line 16 is extremely lowered. Accordingly, a predetermined amount of the sample water can continuously be fed the analysis system even though the flow control valve 22 provided on the outlet line 18 becomes closed due to a lowered pressure of the sample water.

Figure 2:
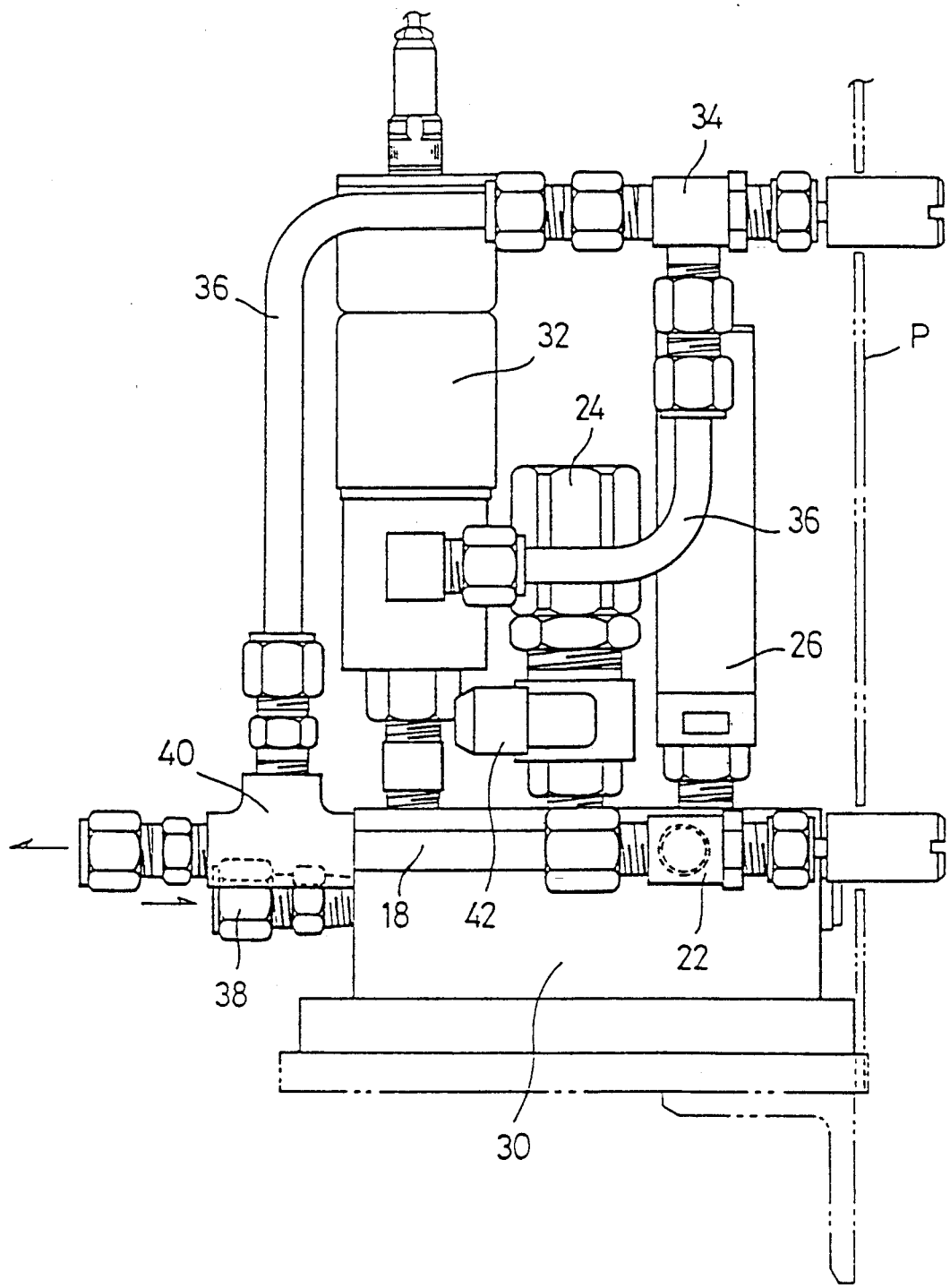
FIG. 2 illustrates a piping structure of the flow control mechanism constituting the control system shown in FIG. 1.

FIG. 2 shows a concrete piping structure including the manifold 30 and bypass line 36 according to one embodiment of the invention shown in FIG. 1. In FIG. 2, the manifold 30 is horizontally arranged on an operator panel P. The manifold 30 is provided on one side face with a connector 38 being used as an inlet part for the sample water, and on the upper side face with the pressure detector 26 and the electromagnetic control valve 32. Further, the outlet line 18 is derived from another side face of the manifold through the flow control valve 22 to the analysis system. The bypass line 36 is derived from one side face of the manifold through the electromagnetic control valve 32 and connected through a fitting 40 to the downstream side of the outlet line 18 derived from the manifold 30. A reference numeral 42 represents a part of a relief pipe being connected to the a relief valve 24.

Thus, according to the present invention, it is possible to miniaturize such a complicated piping structure to save a space for arranging a plurality of lines, by providing the manifold at a part of the outlet line so as to be connected to the control devices and the bypass line 36.

Figure 3:
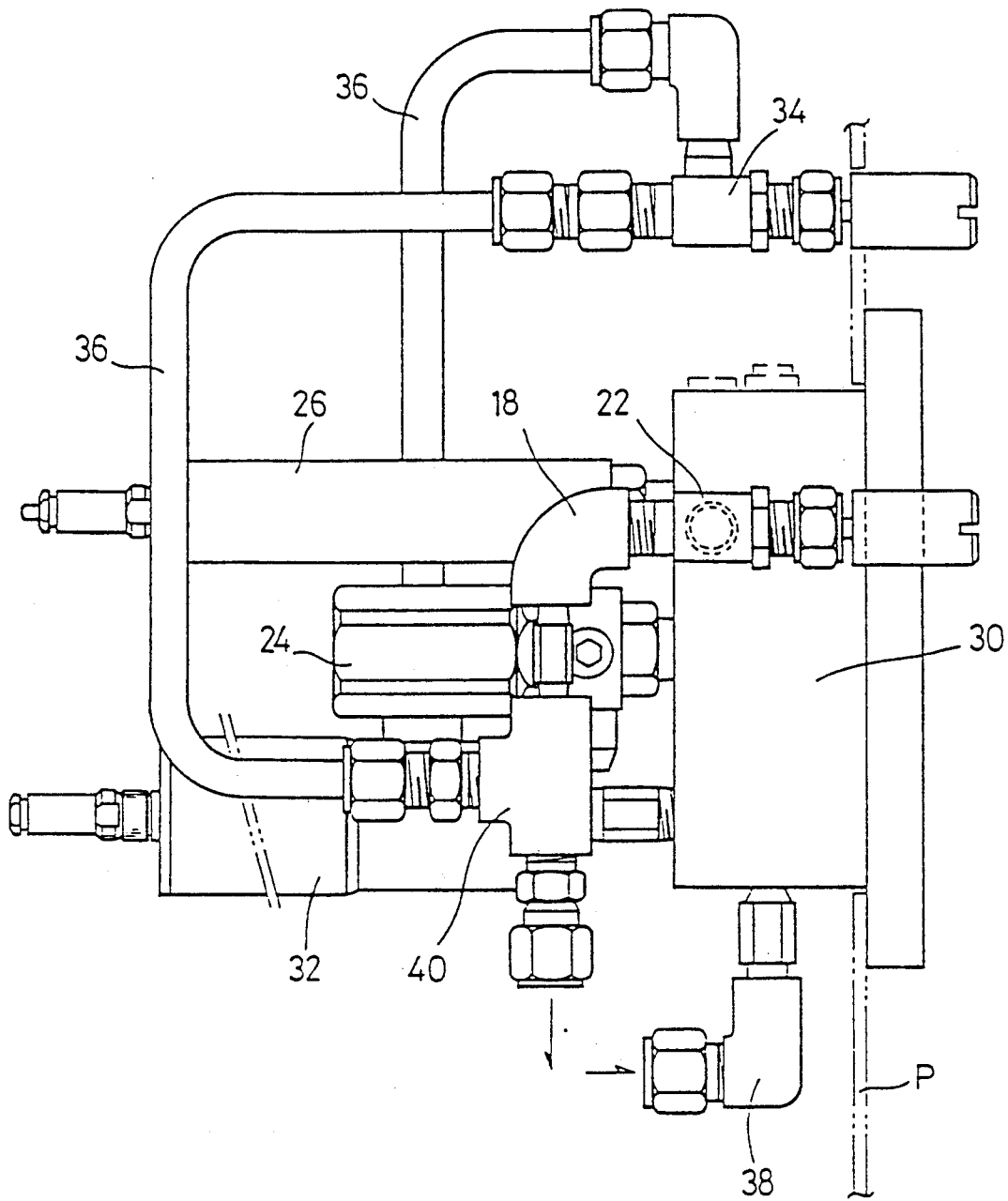
FIG. 3 illustrates a piping structure of the flow control mechanism of another embodiment according to the present invention.

FIG. 3 shows the same piping structure as that shown in FIG. 2 according to another embodiment of the invention. In FIG. 3, the manifold is vertically arranged on the operator panel P. In accordance with this embodiment, as well as the embodiment shown in FIG. 2, a miniaturized and space-saved piping structure can be realized. Therefore, like reference numerals refer to like parts shown in FIG. 2 and the detailed explanation thereof is omitted.

In the embodiments shown in FIGS. 2 and 3, various lines to be connected to the flow control valve 22 and the auxiliary flow control valve 34 are appropriately designed such that the flow control valve 22 and the auxiliary flow control valve 34 are arranged controllably on the operator panel P.

As apparent from the hereinbefore described embodiments according to the invention, there is provided the flow control mechanism for the automatic pressure reducing equipment. The automatic pressure reducing equipment has the pressure reducing mechanism comprising a pair of pressure control tubules parallel to each other, the inlet line for feeding high pressure sample water and the outlet line for discharging pressure-reduced sample water being connected to one end of each of the pressure control tubules and a pair of core rods being inserted into the other end of each of the pressure control tubules, an automatic pressure-reducing control unit for automatically adjusting a position of the core rods to be inserted into the pressure control tubules, and the controller for generating a control command to the automatic pressure-reducing control unit such that a pressure of the sample water being detected in the outlet line is controlled so as to be equal to a preset value after detecting the pressure of the sample water. The flow control mechanism for such an automatic pressure reducing equipment comprises;

the manifold being provided on the outlet line, from a part of which the outlet line is derived and communicates through the main flow control valve with the analysis system for the sample water;

the pressure detector and the relief valve being connected to the manifold;

the bypass line being derived from a part of the manifold and communicating through the electromagnetic control valve and the auxiliary flow control valve with a downstream side of the outlet line being provided with the main flow control valve; and a control means for automatically opening the electromagnetic control valve.

In case the pressure reducing mechanism is rendered inoperable due to a reduction of a pressure of the sample water in the inlet line, the electromagnetic control valve is automatically opened so that the bypass line can be connected to the outlet line in spite of the main flow control valve being closed due to the pressure reduction. Therefore, a predetermined amount of the sample water can be continuously fed to the analysis system.

The automatic control operation for opening the electromagnetic control valve can be performed conveniently and appropriately by the controller and the pressure detector provided on the manifold. The pressure detector detects a pressure of the sample water in the outlet line. In case a detected value of the pressure of the sample water is decreased below a value of the minimum pressure-reducing of the pressure reducing mechanism, the controller generates a control command for opening the electromagnetic control valve.

Moreover, according to the invention, a complicated piping structure can be miniaturized and space-saved by providing the manifold on the outlet so as to be connected with various control devices and a plurality of pipings.

Although the present invention has been described hereinbefore with its preferred embodiments, it will be appreciated that many variations and modifications may be made without departing from the spirit and scope of the invention.

What is claimed is:

1. In automatic pressure reducing equipment comprising a pressure reducing mechanism provided with a pair of pressure control tubules parallel to each other, an inlet line for feeding high pressure sample water and an outlet line for discharging pressure-reduced sample water connected to one end of each of said pressure control tubules and a pair of core rods for pressure reduction inserted into the other end of each of said pressure control tubules, an automatic pressure-reducing control unit for automatically adjusting a position of said core rods to be inserted into said pressure control tubules, a controller for generating a control command to the automatic pressure-reducing control unit such that a pressure of the sample water being detected in said outlet line is controlled so as to be equal to a preset vale after detecting the pressure of the sample water, and a flow control mechanism for the automatic pressure reducing equipment the improvement wherein said flow control mechanism comprises a manifold on said outlet line, from a part of which said outlet line emerges and communicates through a main flow control valve with an analysis system for the sample water;

a pressure detector and a relief valve connected to said manifold;

a bypass line from a part of said manifold and communicating through an electromagnetic control valve and an auxiliary flow control valve with a downstream side of the outlet line having said main flow control valve; and a control means for opening said electromagnetic control valve when said main flow control valve is closed due to a reduction of pressure of the sample water in the outlet line.

* * * * *